United States Patent [19]

Nelson et al.

[11] Patent Number: 4,725,622
[45] Date of Patent: Feb. 16, 1988

[54] MYCOPHENOLIC ACID DERIVATIVES IN THE TREATMENT OF RHEUMATOID ARTHRITIS

[75] Inventors: Peter H. Nelson, Los Altos; Anthony C. Allison; Elsie M. Eugui, both of Belmont; Joseph M. Muchowski, Sunnivale, all of Calif.

[73] Assignee: Syntex (U.S.A.) Inc., Palo Alto, Calif.

[21] Appl. No.: 821,633

[22] Filed: Jan. 23, 1986

[51] Int. Cl.[4] .................... C07D 307/88; A61K 31/44
[52] U.S. Cl. ........................................ 514/469; 549/310
[58] Field of Search .................... 549/310; 514/469

[56] References Cited

U.S. PATENT DOCUMENTS

| | | | |
|---|---|---|---|
| 3,705,894 | 12/1972 | Gerzon et al. | 548/253 |
| 3,777,020 | 12/1973 | Johnson | 514/525 |
| 3,853,919 | 12/1974 | Mori et al. | 548/964 |
| 3,868,454 | 2/1975 | Johnson | 514/228 |
| 3,880,995 | 4/1975 | Jones | 514/27 |
| 3,903,071 | 9/1975 | Holmes | 536/18.1 |

FOREIGN PATENT DOCUMENTS

| | | |
|---|---|---|
| 815330 | 9/1975 | Belgium . |
| 2237549 | 12/1974 | Fed. Rep. of Germany . |
| 48-86860 | 11/1973 | Japan . |
| 57-024380 | 2/1982 | Japan . |
| 57-183776 | 11/1982 | Japan . |
| 57-183777 | 11/1982 | Japan . |
| 1261060 | 1/1972 | United Kingdom . |

OTHER PUBLICATIONS

*J. Antibiotics*, vol. 29, pp. 275–285, pp. 286–291, (1976).
*Cancer Research*, vol. 36, pp. 2923–2927, (1976).

*Primary Examiner*—Jane T. Fan
*Attorney, Agent, or Firm*—Ellen J. Wise; Tom M. Moran

[57] ABSTRACT

A method of treating rheumatoid arthritis which method comprises administering to a mammal in need of such treatment a therapeutically effective amount of a compound of the formula:

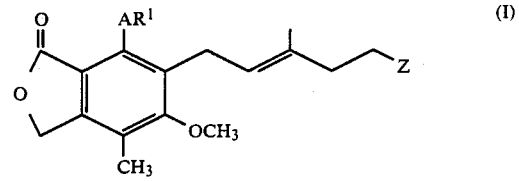

and the pharmaceutically acceptable salts thereof,
wherein:
A is oxygen or sulfur;
$R^1$ is selected from the group consisting of H,

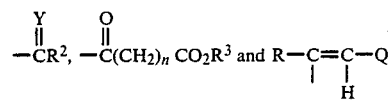

in which
Y is oxygen or sulfur:
$R^2$ is alkyl, haloalkyl or $-NR^4R^5$, where $R^4$ and $R^5$ are independently H, alkyl, haloalkyl, cycloalkyl, phenyl optionally monosubstituted with halogen, hydroxy, carboxy, chlorocarbonyl, sulfonylamino, nitro, cyano, phenyl, alkyl, acyl, alkoxycarbonyl, acylamino, dialkylamino or dialkylaminoethoxycarbonyl, phenyl optionally disubstituted with hydroxy, carboxy, nitro or alkyl, or benzyl optionally substituted with dialkylamino;
n is an integer from 0–6;
$R^3$ is H alkyl or a pharmaceutically acceptable cation;
Q and R are independently H or $-CO_2R^3$; and
Z is selected from the group consisting of $-CH_2OH$, $-CHO$, $-CN$, 1H—tetrazolyl,

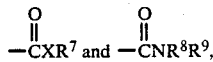

in which
X is oxygen or sulfur,
$R^7$ is H, alkyl, alkenyl, cycloalkyl, optionally substituted phenyl, optionally substituted benzyl or a pharmaceutically acceptable cation; and
$R^8$ and $R^9$ are independently H, alkyl or cycloalkyl, or $R^8$ and $R^9$ taken together are $-(CH_2)_4-$, $-(CH_2)_5-$ or $-(CH_2)_2O(CH_2)_2-$;
with the proviso that $R^1$ and $R^7$ cannot both be H if X and A are oxygen.

15 Claims, No Drawings

MYCOPHENOLIC ACID DERIVATIVES IN THE TREATMENT OF RHEUMATOID ARTHRITIS

BACKGROUND OF THE INVENTION

FIELD OF THE INVENTION

This invention concerns mycophenolic acid derivatives as agents in the treatment of rheumatoid arthritis.

PREVIOUS DISCLOSURES

Rheumatoid arthritis has been treated with a variety of compounds representing many structural classes, including, for example, corticosteroids, aspirin and related compounds, derivatives of arylacetic and arylpropionic acids, relatives of phenylbutazone, gold salts and penicillamine and its derivatives. However, no representative of any of these classes of compounds is regarded as ideal.

Mycophenolic acid is a weakly-active antibiotic found in the fermentation broth of Penicillium brevicompactum. It has now been discovered that certain mycophenolic acid derivatives and related compounds are useful as agents in the treatment of rheumatoid arthritis.

Compounds somewhat structurally similar to the novel compounds of the present invention (compounds illustrated by Formula II as defined herein) are described in U.S. Pat. Nos. 3,705,894; 3,853,919; 3,868,454; 3,880,995, in Japanese Pat. No. J 57024380, in the J. Antibiot., 29(3), 275–85, 286–91 (1976), and in Cancer Research, 36(8), 2923–7 (1976). The disclosed compounds are described as having anti-tumour, immunosuppressive, anti-viral, anti-arthritic and anti-psoriatic activities.

The present invention includes the discovery that the family of compounds illustrated by Formula I and as defined herein are active in biological models of chronic inflammatory diseases, including models of rheumatoid arthritis in mammals. While many of these compounds are disclosed elsewhere, their usefulness in treating rheumatoid arthritis was not previously known. Compounds similar to or included in Formula I are described in U.S. Pat. Nos. 3,705,894, 3,777,020, and 3,868,454, Japanese Kokai Nos. 57/183776, 57/183777, and 48/86860, South African Application No. 68/4959, Great Britain Pat. No. 1261060, Belgian Pat. No. 815330, and West German Pat. No. 2237549.

SUMMARY OF THE INVENTION

In a first aspect, the invention pertains to a method of treating rheumatoid arthritis which method comprises administering to a mammal in need of such treatment a therapeutically effective amount of a compound of the formula:

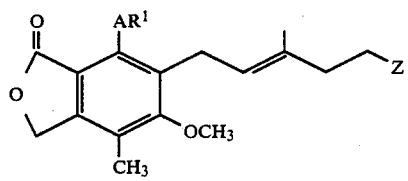

and the pharmaceutically acceptable salts thereof, wherein:
A is oxygen or sulfur;
$R^1$ is selected from the group consisting of H,

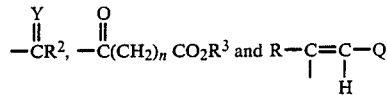

in which
Y is oxygen or sulfur;
$R^2$ is alkyl, haloalkyl or $-NR^4R^5$, where $R^4$ and $R^5$ are independently H, alkyl, haloalkyl, cycloalkyl, phenyl optionally monosubstituted with halogen, hydroxy, carboxy, chlorocarbonyl, sulfonylamino, nitro, cyano, phenyl, alkyl, acyl, alkoxycarbonyl, acylamino, dialkylamino or dialkylaminoethoxycarbonyl, phenyl optionally disubstituted with hydroxy, carboxy, nitro or alkyl, or benzyl optionally substituted with dialkylamino;
n is an integer from 0–6;
$R^3$ is H alkyl or a pharmaceutically acceptable cation;
Q and R are independently H or $-CO_2R^3$; and
Z is selected from the group consisting of $-CH_2OH$, $-CHO$, $-CN$, 1H—tetrazolyl,

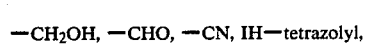

in which
X is oxygen or sulfur;
$R^7$ is H, alkyl, alkenyl, cycloalkyl, optionally substituted phenyl, optionally substituted benzyl or a pharmaceutically acceptable cation; and
$R^8$ and $R^9$ are independently H, alkyl or cycloalkyl, or $R^8$ and $R^9$ taken together are $-(CH_2)_4-$, $-(CH_2)_5-$ or $-(CH_2)_2O(CH_2)_2-$;
with the proviso that $R^1$ and $R^7$ cannot both be H if X and A are oxygen.

In a second aspect, the invention pertains to novel compounds of the formula:

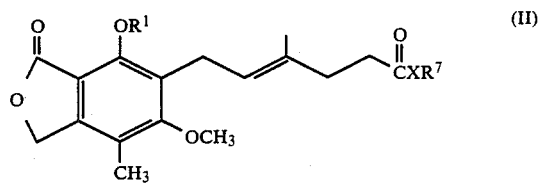

and the pharmaceutically acceptable salts thereof, wherein:
$R^1$ is selected from the group consisting of

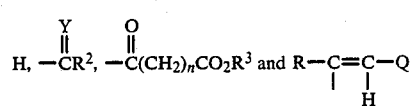

in which
Y is oxygen or sulfur;
$R^2$ is H, alkyl having 1 to 6 carbon atoms or $-NR^4R^5$, where $R^4$ is H or alkyl having 1 to 6 carbon atoms and $R^5$ is H, alkyl having 1 to 6 carbon atoms or

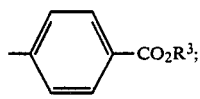

n is an integer from 0-6;

$R^3$ is H, alkyl having 1 to 6 carbon atoms or a pharmaceutically acceptable cation;

Q and R are independently H or —$CO_2R^3$; and

X is oxygen or sulfur; and $R^7$ is H, alkyl having 1 to 6 carbon atoms, cycloalkyl, optionally substituted phenyl, optionally substituted benzyl or a pharmaceutically acceptable cation;

with the proviso that $R^1$ cannot be H or $COR^2$ when X is oxygen.

In two other aspects, the invention relates to a pharmaceutical composition containing a therapeutically effective amount of a compound of Formula II admixed with at least one pharmaceutically acceptable excipient, and to a method of treating rheumatoid arthritis in a mammal by administering to a mammal in need of such treatment a therapeutically effective amount of a compound of Formula II.

Finally, the invention relates to novel processes for preparing the compounds of Formula II and includes the preparation of several novel intermediates.

DETAILED DESCRIPTION OF THE INVENTION

Definitions

As used herein:

"Alkyl" means a branched or unbranched saturated hydrocarbon chain containing 1 to 6 carbon atoms, such as methyl, ethyl, propyl, isopropyl, tert-butyl, butyl, n-hexyl and the like.

"Alkoxy" means the group —OR wherein R is lower alkyl as herein defined. "Cycloalkyl" means cyclopentyl, cyclohexyl or cycloheptyl.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Optionally substituted phenyl", unless otherwise specified, refers to a phenyl moiety optionally bearing one to three substituents independently chosen from the group consisting of halogen, hydroxy, carboxy, chlorocarbonyl, aminosulfonyl, $NO_2$, CN, alkyl having one to six carbon atoms, alkoxycarbonyl, acylamino, and dialkylaminoethoxycarbonyl.

"Optionally substituted benzyl" refers to a benzyl moiety optionally bearing one to three substituent independently selected from the group consisting of halogen, hydroxy, carboxy, chlorocarbonyl, aminosulfonyl, $NO_2$, CN, alkyl having one to six carbon atoms, alkoxycarbonyl, acylamino, and dialkylaminoethoxycarbonyl.

Some compounds of Formula I and II may be converted to a base addition salt by virtue of the presence of a carboxylic acid group. The term "Pharmaceutically acceptable cation" refers to the cation of such salts. The cation is chosen to retain the biological effectiveness and properties of the corresponding free acids and to not be biologically or otherwise undesirable. The cations derived from inorganic bases include sodium, potassium, lithium, ammonium, calcium, magnesium and the like. Cations derived from organic bases include those formed from primary, secondary and tertiary amines, such as isopropylamine, diethylamine, trimethylamine, pyridine, cyclohexylamine, ethylene diamine, monoethanolamine, diethanolamine, triethanolamine and the like.

The compounds of Formulas I and II are derivatives of "mycophenolic acid" which has the structure shown as Formula (III) and has a ring system numbered as shown:

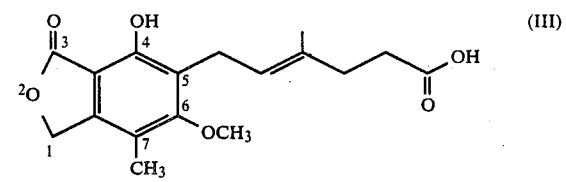

The compounds of the invention will be named using the above shown numbering system as 6-(1,3-dihydro-4-hydroxy-6-methoxy-7-methyl-3-oxo-5-isobenzofuranyl)-4-methyl-4-hexenoic acid derivatives. The symbol "E" designates the configuration of the side chain double bond. Following are examples of how representative compounds of Formulas I and II are named:

The compound of Formula II in which $R^1$ is —$CO(CH_2)_2CO_2C_2H_5$, X is oxygen and $R^7$ is hydrogen, is named "E-6-[1,3-dihydro-4-(3-carboethoxypropionyloxy)-6-methoxy-7-methyl-3-oxo-5-isobenzofuranyl]-4-methyl-4-hexenoic acid".

A compound of Formula II in which $R^1$ is

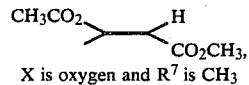

X is oxygen and $R^7$ is $CH_3$ is named "methyl E-6-[1,3-dihydro-4-(1,2-dicarbomethoxyeth-2-(E)-enyloxy)-6-methoxy-7-methyl-3-oxo-5-isobenzofuranyl]-4-methyl-4-hexenoate".

A compound of Formula II in which $R^1$ is —$CYNR^4R^5$ where Y is oxygen, $R^4$ is hydrogen, $R^5$ is 4-carboxyphenyl, X is sulfur and $R^7$ is —$C_2H_5$ is named "ethyl (E)-6-{1,3-dihydro-4-[N-(4-carboxyphenyl)carbamoyloxy]-6-methoxy-7-methyl-3-oxo-5-isobenzofuranyl}-4-methyl-4-thiohexenoate".

Methods of Preparation

The novel compounds of the invention (compounds of Formula II) are prepared by the procedures detailed below and illustrated in Reaction Schemes 1, 2 and 3, and will be variously designated as compounds of Formulas IIA–IIE.

Many of the compounds of the family illustrated by Formula I are known, and their syntheses are available from the published scientific and patent literature. In particular, methods of preparing the compounds of Formula I are described in U.S. Pat. Nos. 3,705,894, 3,777,020, and 3,868,454, Japanese Kokai Nos. 57/183776, 57/183777, and 48/86860, South African Application No. 68/4959, Great Britain Pat. No. 1261060, Belgian Pat. No. 815330, and West German Pat. No. 2237549, the relevant portions of which are incorporated herein by reference. Compounds of Formula which are novel are described herein as compounds of Formula IIA and IIB.

Compounds of Formulas IIA and IIB

The compounds of Formulas IIA and IIB can be prepared as shown in Reaction Scheme 1.

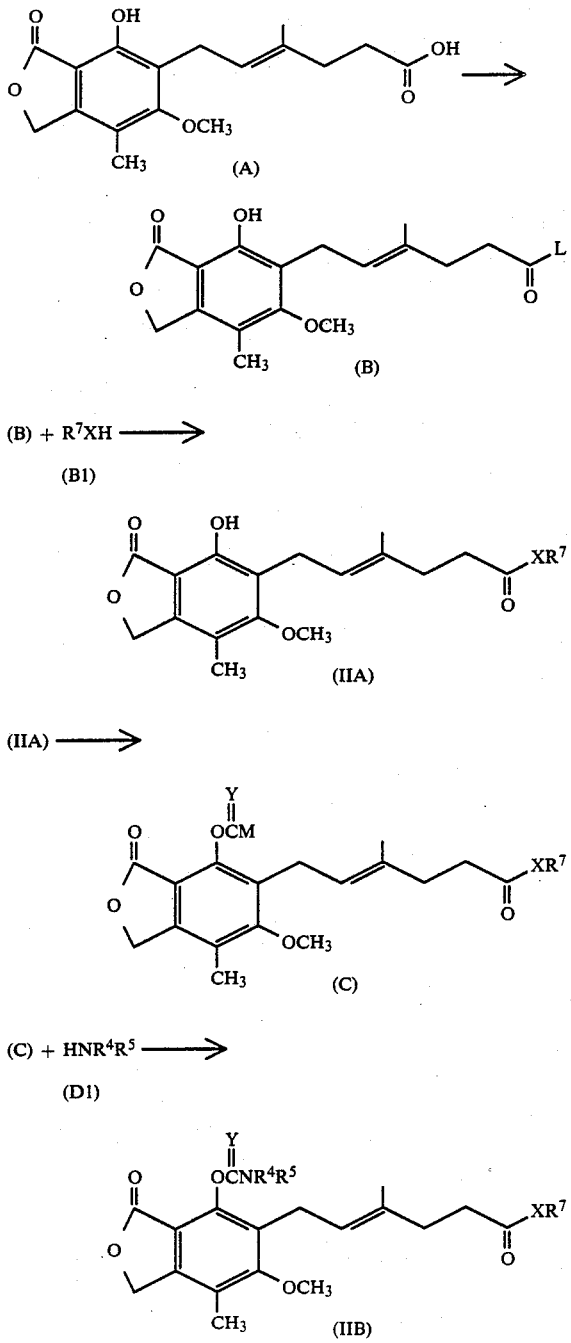

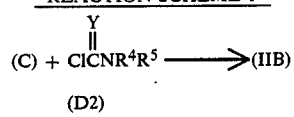

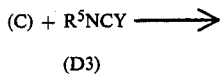

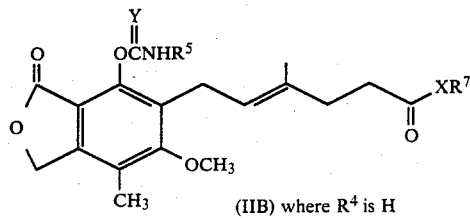

(IIB) where R⁴ is H

As shown in Reaction Scheme 1, the compounds of Formulas IIA (compounds of Formula II in which $R^1$ is hydrogen) and IIB (compounds of Formula II in which $R^1$ is $-CYNR^4R^5$) are prepared from mycophenolic acid (A). To prepare the compounds of Formula IIA, the mycophenolic acid of Formula A is first converted to an activated carbonyl derivative of Formula B in which L is a leaving group such as halo, N-carbonylimidazole, alkoxy, acyloxy or the like, chosen to be capable of displacement by a compound of Formula B1 in the presence of a base. The compounds of Formula B are prepared by standard means well known in the chemical arts. For example, the compound of Formula B where L is chloro is made by reaction with from 1.0 to 10 molar equivalents, preferably 4.0 molar equivalents, of an inorganic acid halide such as phosphorus trichloride, phosphorus pentachloride or preferably thionyl chloride, optionally in the presence of a catalytic amount of an N,N-disubstituted amide, such as N,N-dimethylformamide in an inert organic solvent such as benzene, toluene, acetonitrile, tetrahydrofuran, diethyl ether, chloroform or preferably methylene chloride. The reaction is conducted at a temperature of about 0° to 90° C., preferably about 25° C., for about 1-12 hours, preferably about three hours. Compounds of Formula B in which L is another appropriate leaving group such as those mentioned above can also be readily prepared by well known means. No one leaving group is particularly preferred over others.

The product of Formula B is then reacted with about 1-10 molar equivalents, preferably about 4.0 molar equivalents, of a compound of Formula B1 in an inert organic solvent as defined above, preferably dichloromethane. The reaction takes place in the presence of from 1-10 molar equivalents, preferably about 5 molar equivalents, of an inorganic base such as sodium carbonate, potassium bicarbonate or the like, or a tertiary organic base, such as triethylamine, N-methylpiperidine, or preferably pyridine. The reaction is conducted at 0°-25° C., preferably about 5° C., for thirty minutes to six hours, preferably about one hour. The resulting product of Formula IIA is isolated and purified by conventional means.

The compounds of Formula IIB are prepared from the compounds of Formula IIA by conversion to an activated carbonyl or thiocarbonyl derivative of Formula C, in which M is a leaving group chosen to be capable of displacement by an amine of Formula D1.

For example, M may be halo, N-carbonylimidazole, trichloromethoxy, optionally substituted phenoxy, such as 2,4-dichlorophenoxy, 4-methoxyphenyl, and the like.

The conversion of the compound of Formula IIA to a compound of Formula C is performed by standard means appropriate to the chosen leaving group. For example, the compound of Formula C where M is chloro is made by reaction of the compound of Formula IIA with from 1–10 molar equivalents, preferably about 2 molar equivalents, of phosgene or thiophosgene in an inert organic solvent as defined above, preferably benzene. The reaction takes place in the presence of from 1–5 molar equivalents, preferably about 2 molar equivalents of a tertiary organic base such as triethylamine or preferably pyridine. The reaction is conducted at from 0°–50° C., preferably about 25° C., for about 1–72 hours, preferably about 18 hours, and then filtered. Evaporation of the filtrate under vacuum affords the compound of Formula C where M is chloro.

Alternatively, the compound of Formula IIA is reacted as above, substituting an appropriately substituted alkyl or aryl chloroformate or chlorothioformate for phosgene or thiophosgene, giving the compound of Formula C where M is the correspondingly substituted alkoxy or aryloxy moiety.

Similarly, the compound of Formula IIA can be reacted as above, substituting N,N'-carbonyldiimidazole or N,N'-thiocarbonyldiimidazole for phosgene or thiophosgene, giving the compound of Formula C where M is N-carbonylimidazole or N-thiocarbonylimidazole.

The products of the reactions described herein can be isolated and purified by any suitable separation or purification procedure, such as, for example, filtration, extraction, crystallization, column chromatography, thin-layer chromatography, thick-layer chromatography, preparative low or high pressure liquid chromatography, or a combination of these procedures. Specific illustrations are described in the Examples. However, other equivalent separation or purification procedures can be used.

The salt products are also isolated by conventional means. For example, the reaction mixtures can be evaporated to dryness and the salts then further purified by standard methods such as those listed above.

The compounds of Formula C are then converted to the desired compounds of Formula II by treating with the appropriate reagent, as decribed below.

Compounds of Formula IIB can be prepared by treating the appropriately substituted compound of Formula C with an appropriate amine of Formula D1, as shown, thereby converting the -OCYM group to the corresponding carbamate or thiocarbamate. To carry out this process, the compound of Formula C is dissolved in an inert organic solvent as defined above, preferably tetrahydrofuran, and reacted with from about 2–5 molar equivalents, preferably about 2–3 molar equivalents, of the appropriate amine of Formula D1 in solution in an inert solvent as defined above, preferably tetrahydrofuran. The reaction takes place at a temperature of about 0°–40° C., preferably about 25° C., for about 1–10 hours, preferably about 4 hours, at a pressure of about 1–5 atmospheres, preferably at atmospheric pressure. When the reaction is substantially complete, the product compound of Formula II is isolated by conventional means and if desired converted to a pharmaceutically acceptable salt.

Alternatively, the reaction is carried out in the presence of from 1–5 molar equivalents, preferably 2 molar equivalents, of a tertiary organic base or an inorganic base, as defined above. The compound of Formula C is reacted with from 1–4 molar equivalents, preferably about 1.2 molar equivalents, of the appropriate amine of Formula D1 in an inert organic solvent, as defined above.

Alternatively, compounds of Formula IIB are made directly from compounds of Formula C, by reaction with an appropriately substituted carbamoyl or thiocarbamoyl chloride or Formula D2. To carry out this process, the compound of Formula C is dissolved in an inert organic solvent as defined above, preferably tetrahydrofuran, and reacted with from 1–4 molar equivalents, preferably about 1.2 molar equivalents, of the appropriate carbamoyl or thiocarbamoyl chloride of Formula D2 in the presence of a tertiary organic base or inorganic base as defined above. The reaction takes place at a temperature of about 0°–40° C., preferably about 25° C., for about 1–10 hours, preferably about 4 hours. When the reaction is substantially complete, the product of Formula IIB is isolated by conventional means.

Compounds of Formula IIB where $R^4$ is H can also be made by reacting a compound of Formula C with an appropriately substituted isocyanate or isothiocyanate of Formula D3. To carry out this process, the compound of Formula C is dissolved in an inert organic solvent as defined above, preferably toluene, and reacted with from 1–5 molar equivalents, preferably about 2 molar equivalents, of an isocyanate or isothiocyanate of Formula D3. The reaction takes place at a temperature of about 10°–100° C., preferably about 50° C., for about 1–10 hours, preferably about 4 hours. When the reaction is substantially complete, the product of Formula IIB is isolated by conventional means.

Compounds of Formulas IIC and IID

The preparation of compounds of Formula IIC (compounds of Formula II in which $R^1$ is $-COR^2$ and $R^2$ is alkyl), and Formula IID (compounds of Formula II in which $R^1$ is $-CO(CH_2)_nCO_2R^3$ is shown in Reaction Scheme 2.

REACTION SCHEME 2

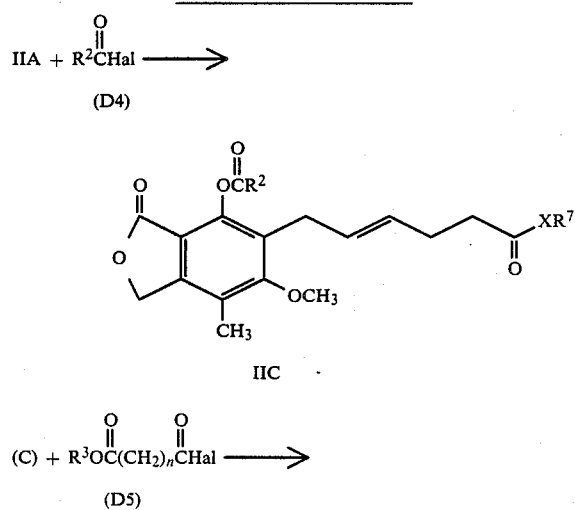

-continued
REACTION SCHEME 2

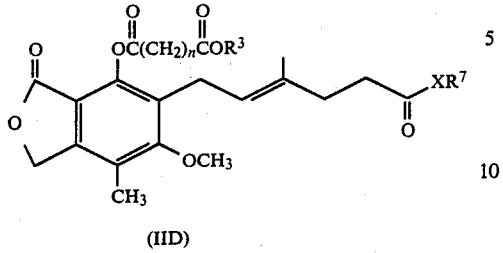

(IID)

-continued
REACTION SCHEME 3

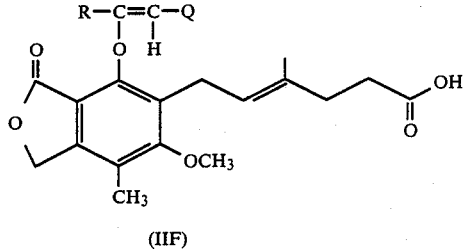

(IIF)

The compounds of Formula IIC are prepared directly from compounds of Formula IIA by reaction with an appropriately substituted acyl halide of Formula D4. To carry out this process, the compound of Formula IIA is dissolved in an inert organic solvent as defined above, preferably acetonitrile, and reacted with about 1 to 6 molar equivalents, preferably about 3 molar equivalents, of the appropriate compound of Formula D4, in the presence of about 1 to 6 molar equivalents, preferably about 3 molar equivalents, of an inorganic base or tertiary organic base as defined above, preferably pyridine. The reaction takes place at a temperature of about 0°–25° C., preferably about 5° C., for about 1–10 hours, preferably about 3 hours. When the reaction is substantially complete, the product of Formula IIC is isolated by conventional means.

Similarly, substituting an acyl halide of Formula D5 for an acyl halide of Formula D4, the compounds of Formula IID are prepared. Compounds of Formula IID where —XR$^7$ is OH are prepared by carrying out the above reaction directly on mycophenolic acid, the compound of Formula A.

Compounds of Formulas IIE and IIF

Compounds of Formula IIE (compounds of Formula II in which R$^1$ is R—C=C—Q) and Formula IIF (compounds of Formula II in which R$^1$ is R—C=C—Q, in which R and Q are H or —CO$_2$R$^3$, where R$^3$ is H, are prepared as shown in Reaction Scheme 3, below.

REACTION SCHEME 3

(IIA) + R—C≡C—Q ——→
(D6)

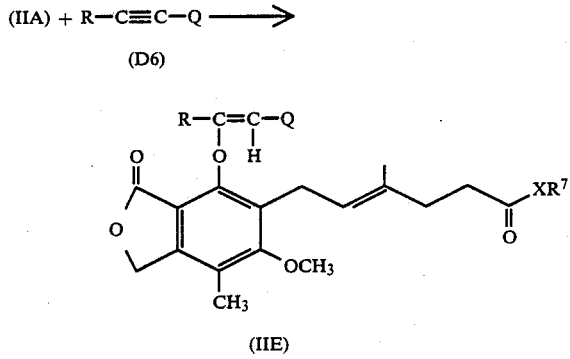

(IIE)

IIE ——→

Compounds of Formula IIE are prepared directly from compounds of Formula IIA by reaction with an appropriately substituted acetylene of Formula D6. To carry out this process, the compound of Formula C is dissolved in an inert organic solvent as defined above, preferably tetrahydrofuran, and reacted with about 1 to 5 molar equivalents, preferably about 2 molar equivalents, of the appropriate compound of Formula D6 in the presence of about 1 to 5 molar equivalents, preferably about 2 molar equivalents, of a tertiary organic base or inorganic base as defined above, preferably pyridine. The reaction takes place at a temperature of about 0°–50° C., preferably about 5° C., for about 1–48 hours, preferably about 16 hours. When the reaction is substantially complete, the product of Formula IIE is isolated by conventional means.

Compounds of Formula IIF are prepared by hydrolysis of compounds of Formula IIE. To carry out the process, the compound of Formula IIE is dissolved in an inert organic solvent as defined above, preferably tetrahydrofuran, and reacted with about 3 to 15 molar equivalents, preferably about 6 molar equivalents, of an inorganic base such as sodium hydroxide, potassium carbonate, or preferably lithium hydroxide, dissolved in a protic solvent such as methanol, ethanol or preferably water. The reaction takes place at a temperature of about 0°–50° C., preferably about 25° C., for about 1–48 hours, preferably about 20 hours. When the reaction is substantially complete, the product of Formula IIF is isolated by conventional means.

Salts of Compounds of Formula II

Some of the compounds of Formula II may be converted to corresponding base addition salts by virtue of the presence of a carboxylic acid group. The conversion is accomplished by treatment with a stoichiometric amount of an appropriate base, such as potassium carbonate, sodium bicarbonate, ammonia, ethylenediamine, monoethanolamine, diethanolamine, triethanolamine and the like. Typically, the free acid is dissolved in a polar organic solvent such as ethanol or methanol, and the base added in water, ethanol or methanol. The temperature is maintained at 0°–50° C. The resulting salt precipitates spontaneously or may be brought out of solution with a less polar solvent.

The base addition salts of the compounds of Formula II may be decomposed to the corresponding free acids by treating with an exess of a suitable acid, such as hydrochloric acid or sulfuric acid, typically in the presence of aqueous solvent, and at a temperature of between 0° and 50° C. The free acid form is isolated by conventional means, such as extraction with an organic solvent.

Preparation of Starting Materials

The compounds of Formula II are prepared from mycophenolic acid, the compound of Formula A, which is commercially available.

The compounds of Formula B1 and Formula D1 are commercially available, or can be prepared by standard methods known to those skilled in the chemical art. The compounds of Formula B1 which are not commercially available are prepared by means well known to those skill in the art, for example as described in *Synthetic Organic Chemistry* by Wagner and Zook, pp. 148–225 and 778–786, which is incorporated herein by reference. In general, the compounds of Formula D1 are commercially available. The compounds of Formula D1 wherein $R^5$ is phenyl having a substituent $COOR_3$ where $R^3$ is lower alkyl are prepared from the compounds of Formula D1 where $R_3$ is H—for example, by reaction of the appropriate compound of Formula D1 with an excess of the alcohol $R_3OH$ in the presence of an acid catalyst. The reaction is described in greater detail in *Organic Functional Group Preparations*, 2nd Edition, Vol. I, by Sandler and Karo, pp. 289–309, which is incorporated herein by reference.

The compounds of Formula D2 are either available commercially or can be prepared by, for example, reaction of a secondary amine of Formula D1 with phosgene (Y=O) or thiophosgene (Y=S). Compounds of Formula D2 wherein $R_1$ is H can be prepared by the reaction of an isocyanate or isothiocyanate of Formula D3 with an excess of dry hydrochloric acid in an inert solvent. These reactions are described in greater detail in *Comprehensive Organic Chemistry*, Vol. 2, by Barton and Ollis, pp. 1088–1090, which is incorporated herein by reference.

Any alkyl or aryl chloroformates or chlorothioformates that are not commercially available are prepared, for example, by reaction of phosgene or thiophosgene with one equivalent of the appropriate alcohol or phenol in the presence of a base. The reactions are described in greater detail in *Comprehensive Organic Chemistry*, by Barton and Ollis, Vol 2, pp. 1078–1083 and Vol 3, pp. 432–4, which is incorporated herein by reference.

The compounds of Formula D3 that are not commercially available are prepared by reaction of an appropriately substituted primary amine ($R_2NH_2$) with phosgene or thiophosgene. The reaction is discussed in further detail in *Organic Functional Group Preparations*, 2nd Edition, Vol. 1, by Sandler and Karo, pp. 364–365, which is incorporated herein by reference.

The acyl halides of Formula D4 and Formula D5 are prepared from commercially available carboxylic acids or half esters of dicarboxylic acids respectively. For example, the compounds where M is Cl can be prepared by reaction with thionyl chloride in an inert solvent. The reaction is discussed in further detail in *Synthetic Organic Chemistry*, by Wagner and Zook, pp. 546–547, which is incorporated herein by reference. The half esters of dicarboxylic acids, if not commercially available, can be prepared, for example, by the reaction of the appropriate alcohol and an anhydride formed from a dicarboxylic acid as shown in the reaction scheme below.

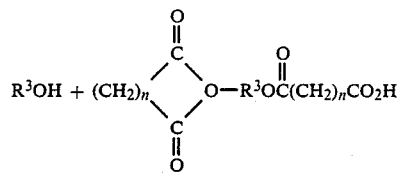

The reaction is discussed in more detail in *Comprehensive Organic Chemistry*, Vol. 2, by Barton and Ollis, p 687, which is incorporated herein by reference.

Acetylenes of Formula D6 are commercially available or are prepared from propiolic acid or acetylene dicarboxylic acid by conventional esterification procedures, which are discussed in more detail in *Organic Functional Group Preparations*, 2nd Edition, Vol 1, by Sandler and Karo, pp 289–309, which is incorporated herein by reference.

In summary, the compounds of the present invention are made by the procedures outlined below:

(1) The process for preparing compounds of Formula IIA comprises reacting a compound of the formula

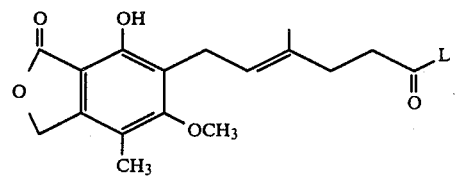

in which L is a leaving group with a compound of the formula $R^7XH$, where $R^7$ and X are as previously defined.

(2) The process for preparing compounds of Formula IIB comprises:

(a) reacting a compound of the formula:

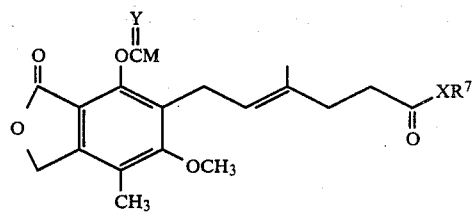

wherein X, Y, M and $R^7$ are as defined above, with an appropriate amine of the formula $R^4R^5NH$, wherein $R^4$ and $R^5$ are as defined above; or (b) converting the free acid, where appropriate, of the compound of Formula IIB with a base to a pharmaceutically acceptable salt; or (c) converting a base addition salt of the compound of Formula IIB with an acid to the corresponding free acid.

(d) converting a base addition salt of the compound of Formula IIB to another pharmaceutically acceptable base addition salt.

(3) Alternatively, a process for preparing a compound of Formula IIB, above, comprises:

(a) reacting a copound of the formula:

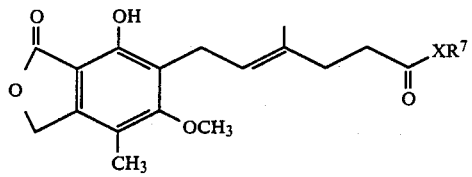

where X and R⁷ are as defined above with a carbamoyl chloride of the formula $R^4R^5NCYCl$, or an isocyanate of the formula $R^5NCY$, wherein $R^4$, $R^5$ and Y are as defined above; or (b) converting the free acid, where appropriate, of the compound of Formula IIB with a base to a pharmaceutically acceptable salt; or (c) converting a base addition salt of the compound of Formula IIB with an acid to the corresponding free acid.

(d) converting a base addition salt of the compound of Formula IIB to another pharmaceutically acceptable base addition salt.

(4) The process for preparing a compound of Formula IIC and Formula IID comprises:

(a) reacting a compound of the formula:

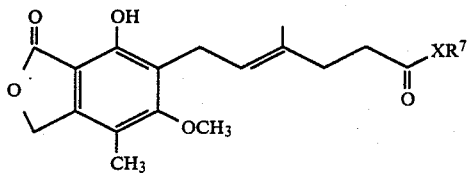

where X and R⁷ are as defined above with an acyl halide of the formula $R^2COHal$; or (b) converting the free acid, where appropriate, of the compound of Formula IIC or Formula IID with a base to a pharmaceutically acceptable salt; or (c) converting a base addition salt of the compound of Formula IIC or Formula IID with an acid to the corresponding free acid.

(d) converting a base addition salt of the compound of Formula IIC or Formula IID to another pharmaceutically acceptable base addition salt.

(5) The process for preparing a compound of Formula IIE comprises:

(a) reacting a compound of the formula

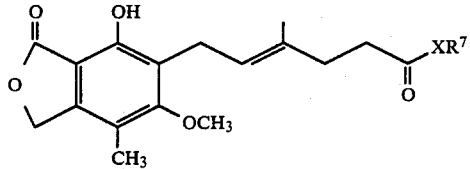

where X and R⁷ are as defined above, with an acetylene of formula $R-C\equiv C-Q$, where R and Q are as defined above; or (b) converting the free acid, where appropriate, of the compound of Formula IIE with a base to a pharmaceutically acceptable salt; or (c) converting a base addition salt of the compound of Formula IIE with an acid to the corresponding free acid.

(d) converting a base addition salt of the compound of Formula IIE to another pharmaceutically acceptable base addition salt.

(6) The process for preparing a compound of Formula IIF comprises:

(a) reacting a compound of the formula:

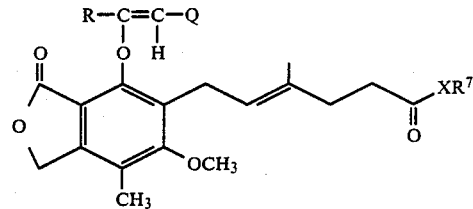

where R and Q are $-CO_2R^3$, where $R^3$ is alkyl having from 1-6 carbon atoms and X and R⁷ are as defined above, with an alkali metal hydroxide followed by a mineral acid; or (b) converting the free acid of the compound of Formula IIF with a base to a pharmaceutically acceptable salt; or (c) converting a base addition salt of the compound of Formula IIF with an acid to the corresponding free acid.

(d) converting a base addition salt of the compound of Formula IIF to another pharmaceutically acceptable base addition salt.

UTILITY AND ADMINISTRATION

The compounds of Formulas I and II have been shown in standard laboratory tests to be useful in treating chronic inflammatory diseases, including models of rheumatoid arthritis, in mammals. Accordingly, the compounds of Formula I and II, their salts, and pharmaceutical compositions containing them, may be used in treating inflammatory diseases with an immunologically based component, particularly rheumatoid arthritis, in mammals by administering a therapeutically effective amount of a compound of Formula I or II to a mammal in need thereof. Anti-inflammatory activity can be determined by the method described by C. M. Pearson in *Proc. Soc. Exp. Biol. Med.*, 91:95-101, (1956) utilizing adjuvant-induced arthritis in rats. This method is described in detail in Example 14 hereinbelow. Rheumatoid arthritis is also characterized as an autoimmune disease. Activity against autoimmune diseases can be determined by the method described by Grieg, et al. in *J. Pharmacol. Exp. Ther.* 173:85 (1970) using experimental allergic encephalomyelitis induced in rats. The method is described in Example 15 below.

Administration of the active compounds and salts described herein can be effected via any medically acceptable mode of administration for agents which control inflammation, rheumatoid arthritis and associated pain. These methods include but are not limited to oral, parenteral and otherwise systemic and topical routes of administration. Oral administration is preferred, depending of course, on the disorder being treated. The compounds are administered in a therapeutically effective amount either alone or in combination with a suitable pharmaceutically acceptable excipient.

Depending on the intended mode of administration, the compounds of this invention may be incorporated in any pharmaceutically acceptable dosage form, such as, for example, tablets, suppositories, pills, capsules, powders, liquids, suspensions, emulsions, aerosols, or the like. Preferably means of administration are unit dosage forms suitable for single administration of precise dosages, or sustained release dosage forms for continuous administration. Preferably the dosage form will include a pharmaceutically acceptable excipient and an active compound of Formula I, or a pharmaceutically acceptable salt thereof, and, in addition, may include other medicinal agents, pharmaceutical agents, carriers, excipients, adjuvants, stabilizers, etc. Depending on parameters such as mode of administration, type of composition, and activity of the compound, the pharmaceutical composition may contain 1-95 percent by weight active ingredient with the remainder being excipient.

For solid dosage forms, non-toxic solid carriers include but are not limited to, for example, pharmaceutical grades of mannitol, lactose, starch, magnesium stearate, sodium saccharin, the polyalkylene glycols, talcum, cellulose, glucose, sucrose, and magnesium carbonate. An example of a solid dosage form of the compounds of this invention is a suppository containing propylene glycol as the carrier. Liquid pharmaceutically administerable dosage forms can, for example, comprise a solution or suspension of an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition or formulation to be administered will, in any event, contain a quantity of the active compound(s) in an amount effective to alleviate the symptoms of the subject being treated.

For oral administration, a pharmaceutically acceptable non-toxic dosage form may contain any of the normally employed excipients, such as, for example pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like. Such dosage forms may contain 1%-95% active ingredient, preferably 25-70%.

For topical administration, an appropriate dosage form will comprise an effective amount of a compound of Formula I in admixture with a pharmaceutically acceptable non-toxic carrier. A suitable range of composition would be 0.1%-10%, preferably 1-2% by weight, active ingredient, and the balance carrier. The concentration of active ingredient in pharmaceutical compositions suitable for topical application will vary depending upon the therapeutic activity of the particular active ingredient and the medical condition to be treated. Suitable dosage forms for topical application of the compounds of this invention include but are not limited to creams, ointments, lotions, emulsions and solutions.

For example, a suitable ointment for topical application of compounds of the instant invention may contain 15-45% by weight of a saturated fatty alcohol having 16 to 24 carbon atoms, such as cetyl alcohol, stearyl alcohol, behenyl alcohol, and the like, and 45-85% by weight of a glycol solvent such as propylene glycol, polyethylene glycol, dipropylene glycol, and mixtures thereof. In addition, the ointment may contain 0-25% by weight of a plasticizer (e.g. polyethylene glycol, 1,2,6-hexanetriol, sorbitol, glycerol, and the like), 0-15% by weight of a coupling agent such as a saturated fatty acid having from 16 to 24 carbon atoms, (e.g., stearic acid, palmitic acid or behenic acid) a fatty acid amide (e.g. oleamide, palmitamide, stearamide of behenamide) or an ester of a fatty acid having from 16 to 24 carbon atoms (e.g., sorbitol monostearate, polyethylene glycol monostearate, polypropylene glycol or the corresponding mono-ester or other fatty acids such as oleic acid and palmitic acid), and 0-20% by weight of a penetrant such as dimethyl sulfoxide of dimethylacetamide.

The amount of active compound administered will, of course, depend on the subject being treated, the severity of the affliction, the manner of administration and the judgment of the prescribing physician. However, a therapeutically effective dosage of compounds of the instant invention is in the range of 1-100 mg/kg/day, preferably about 5-30 mg/kg/day, and most preferably about 10 mg/kg/day. For an average 70 kg human, this would amount to 70 mg-7 g per day, or preferably about 700 mg/day.

Preferred Embodiments

Among the family of compounds defined by Formula I, preferred methods of treating rheumatoid arthritis utilize compounds of Formula I in which A is oxygen and $R^1$ is $CONR^4R^5$. Of these, more preferred methods utilize compounds of Formula I in which Z is $COOR^7$ in which $R^7$ is lower alkyl, particularly hydrogen or methyl.

Among the family of compounds defined by Formula II, one preferred group includes those compounds of Formula II in which X is oxygen. Of these, a preferred subgroup are compound of Formula II in which $R^7$ is hydrogen or methyl. Within this subgroup, one preferred subclass includes compounds of Formula II in which $R^1$ is $CO(CH_2)_nCO_2R^3$, especially those in which $R^3$ is methyl or ethyl. A second preferred subclass within this subgroup includes compounds of Formula II in which $R^1$ is R—C≡CH—Q, particularly those in which R and Q are each $CO_2R^3$ where $R^3$ is hydrogen, methyl or ethyl.

A second preferred group are compounds of Formula II in which X is sulfur. Within this group, a preferred subgroup includes compounds of Formula II in which $R^1$ is hydrogen or $COR^2$, especially where $R^2$ is $—NR^4R^5$.

At present, the most preferred compounds of Formula II are:

(E)-6-[1,3-dihydro-4-(3-carbomethoxypropionyloxy)-6-methoxy-7-methyl-3-oxo-5-isobenzofuranyl]-4-methyl-4-hexenoic acid;

(E)-6-[1,3-dihydro-4-(3-carboethoxypropionyloxy)-6-methoxy-7-methyl-3-oxo-5-isobenzofuranyl]-4-methyl-4-hexenoic acid;

(E)-6-[1,3-dihydro-4-(2-carbomethoxyethanoyloxy)-6-methoxy-7-methyl-3-oxo-5-isobenzofuranyl]-4-methyl-4-hexenoic acid;

(E)-6-[1,3-dihydro-4-(4-carbomethoxybutanoyloxy)-6-methoxy-7-methyl-3-oxo-5-isobenzofuranyl]-4-methyl-4-hexenoic acid;

(E)-6-[1,3-dihydro-4-(5-carbomethoxypentanoyloxy)-6-methoxy-7-methyl-3-oxo-5-isobenzofuranyl]-4-methyl-4-hexenoic acid;

methyl (E)-[1,3-dihydro-4-(1,2-dicarbomethoxyeth-2-(E)-enyloxy)-6-methoxy-7-methyl-3-oxo-5-isobenzofuranyl]-4-methyl-4-hexenoate; and methyl (E)-[1,3-dihydro-4-(1,2-dicarboethoxyeth-2-(E)-enyloxy)-6-methoxy-7-methyl-3-oxo-5-isobenzofuranyl]-4-methyl-4-hexenoate.

The following examples serve to further illustrate the invention. They are not intended, nor should they be construed, to narrow or limit the scope of the invention as claimed.

EXAMPLE 1

Preparation of ethyl (E)-6-(1,3-dihydro-4-hydroxy-6-methoxy-7-methyl-3-oxo-5-isobenzofuranyl)-4-methyl-4-thiohexenoate and related compounds of Formula IIA (a) To a solution of 5.0 g of mycophenolic acid in 75 ml of methylene chloride was added 5 ml of thionyl chloride and 5 drops of N,N-dimethylformamide. The mixture was stirred overnight at 25° C. and the solvent removed under reduced pressure. The residue was dissolved in 100 ml of methylene chloride, cooled to 50° C. and 4.2 ml of pyridine and 5.43 ml of ethylmercaptan added. The mixture was stirred at 25° C. overnight, then poured into water and extracted with methylene chloride. The organic layer was dried over anhydrous magnesium sulfate, evaporated under reduced pressure and the residue chromatographed on silica gel, eluting with a 1:1 mixture of diethyl ether and hexane. The purified product was recrystallized from a mixture of diethyl ether and hexane to yield ethyl (E)-6-(1,3-dihydro-4-hydroxy-6-methoxy-7-methyl-3-oxo-5-isobenzofuranyl)-4-methyl-4-thiohexenoate, having a melting point of 63°–67° C.

(b) Following the procedure described in paragraph (a) above, but using the appropriate compounds of Formula B1, the following compound of Formula IIA was prepared:

Benzyl (E)-6-(1,3-dihydro-4-hydroxy-6-methoxy-7-methyl-3-oxo-5-isobenzofuranyl)-4-methyl-4-thiohexenoate, m.p. 80°–82° C.

(c) In a similar manner, the following compounds of Formula IIA where X is sulfur are prepared:

methyl (E)-6-(1,3-dihydro-4-hydroxy-6-methoxy-7-methyl-3-oxo-5-isobenzofuranyl)-4-methyl-4-thiohexenoate;

propyl (E)-6-(1,3-dihydro-4-hydroxy-6-methoxy-7-methyl-3-oxo-5-isobenzofuranyl)-4-methyl-4-thiohexenoate;

isopropyl (E)-6-(1,3-dihydro-4-hydroxy-6-methoxy-7-methyl-3-oxo-5-isobenzofuranyl)-4-methyl-4-thiohexenoate;

butyl (E)-6-(1,3-dihydro-4-hydroxy-6-methoxy-7-methyl-3-oxo-5-isobenzofuranyl)-4-methyl-4-thiohexenoate;

sec-butyl (E)-6-(1,3-dihydro-4-hydroxy-6-methoxy-7-methyl-3-oxo-5-isobenzofuranyl)-4-methyl-4-thiohexenoate;

n-pentyl (E)-6-(1,3-dihydro-4-hydroxy-6-methoxy-7-methyl-3-oxo-5-isobenzofuranyl)-4-methyl-4-thiohexenoate;

n-hexyl (E)-6-(1,3-dihydro-4-hydroxy-6-methoxy-7-methyl-3-oxo-5-isobenzofuranyl)-4-methyl-4-thiohexenoate;

cyclohexyl (E)-6-(1,3-dihydro-4-hydroxy-6-methoxy-7-methyl-3-oxo-5-isobenzofuranyl)-4-methyl-4-thiohexenoate;

cyclopentyl (E)-6-(1,3-dihydro-4-hydroxy-6-methoxy-7-methyl-3-oxo-5-isobenzofuranyl)-4-methyl-4-thiohexenoate;

phenyl (E)-6-(1,3-dihydro-4-hydroxy-6-methoxy-7-methyl-3-oxo-5-isobenzofuranyl)-4-methyl-4-thiohexenoate;

2-chlorophenyl (E)-6-(1,3-dihydro-4-hydroxy-6-methoxy-7-methyl-3-oxo-5-isobenzofuranyl)-4-methyl-4-thiohexenoate;

4-chlorophenyl (E)-6-(1,3-dihydro-4-hydroxy-6-methoxy-7-methyl-3-oxo-5-isobenzofuranyl)-4-methyl-4-thiohexenoate;

4-methoxyphenyl (E)-6-(1,3-dihydro-4-hydroxy-6-methoxy-7-methyl-3-oxo-5-isobenzofuranyl)-4-methyl-4-thiohexenoate; and 2,4-dimethoxyphenyl (E)-6-(1,3-dihydro-4-hydroxy-6-methoxy-7-methyl-3-oxo-5-isobenzofuranyl)-4-methyl-4-thiohexenoate.

(d) Similarly, by following the procedure of part (a) but substituting the appropriate alkyl, cycloalkyl, benzyl alcohol or phenol for the mercaptan, the following compounds of Formula IIA, where X is oxygen, are prepared:

ethyl (E)-6-(1,3-dihydro-4-hydroxy-6-methoxy-7-methyl-3-oxo-5-isobenzofuranyl)-4-methyl-4-hexenoate;

methyl (E)-6-(1,3-dihydro-4-hydroxy-6-methoxy-7-methyl-3-oxo-5-isobenzofuranyl)-4-methyl-4-hexenoate;

propyl (E)-6-(1,3-dihydro-4-hydroxy-6-methoxy-7-methyl-3-oxo-5-isobenzofuranyl)-4-methyl-4-hexenoate;

isopropyl (E)-6-(1,3-dihydro-4-hydroxy-6-methoxy-7-methyl-3-oxo-5-isobenzofuranyl)-4-methyl-4-hexenoate;

butyl (E)-6-(1,3-dihydro-4-hydroxy-6-methoxy-7-methyl-3-oxo-5-isobenzofuranyl)-4-methyl-4-hexenoate;

sec-butyl (E)-6-(1,3-dihydro-4-hydroxy-6-methoxy-7-methyl-3-oxo-5-isobenzofuranyl)-4-methyl-4-hexenoate;

n-pentyl (E)-6-(1,3-dihydro-4-hydroxy-6-methoxy-7-methyl-3-oxo-5-isobenzofuranyl)-4-methyl-4-hexenoate;

n-hexyl (E)-6-(1,3-dihydro-4-hydroxy-6-methoxy-7-methyl-3-oxo-5-isobenzofuranyl)-4-methyl-4-hexenoate;

cyclohexyl (E)-6-(1,3-dihydro-4-hydroxy-6-methoxy-7-methyl-3-oxo-5-isobenzofuranyl)-4-methyl-4-hexenoate;

cyclopentyl (E)-6-(1,3-dihydro-4-hydroxy-6-methoxy-7-methyl-3-oxo-5-isobenzofuranyl)-4-methyl-4-hexenoate;

phenyl (E)-6-(1,3-dihydro-4-hydroxy-6-methoxy-7-methyl-3-oxo-5-isobenzofuranyl)-4-methyl-4-hexenoate;

2-chlorophenyl (E)-6-(1,3-dihydro-4-hydroxy-6-methoxy-7-methyl-3-oxo-5-isobenzofuranyl)-4-methyl-4-hexenoate;

4-chlorophenyl (E)-6-(1,3-dihydro-4-hydroxy-6-methoxy-7-methyl-3-oxo-5-isobenzofuranyl)-4-methyl-4-hexenoate;

4-methoxyphenyl (E)-6-(1,3-dihydro-4-hydroxy-6-methoxy-7-methyl-3-oxo-5-isobenzofuranyl)-4-methyl-4-hexenoate; and 2,4-dimethoxyphenyl (E)-6-(1,3-dihydro-4-hydroxy-6-methoxy-7-methyl-3-oxo-5-isobenzofuranyl)-4-methyl-4-hexenoate.

EXAMPLE 2

Preparation of ethyl (E)-6-(1,3-dihydro-4-carbamoyloxy-6-methoxy-7-methyl-3-oxo-5-isobenzofuranyl)-4-methyl-4-thiohexenoate and related compounds of Formula IIB (a) To a solution of 500 mgs of ethyl (E)-6-(1,3-dihydro-4-hydroxy-6-methoxy-7-methyl-3-oxo-5-isobenzofuranyl)-4-methyl-4-thiohexenoate in 10 ml of benzene cooled in an ice bath was added 0.1 ml of pyridine and 6 ml of a 12.5% solution of phosgene in benzene. The solution was stirred at 25° C. overnight, the precipitate filtered off and solvent removed from the filtrate under reduced pressure. The residue was dissolved in 5 ml of tetrahydrofuran and to this solution was added dropwise a solution of ammonia in tetrahydrofuran until the reaction was complete. The mixture was poured into water and extracted with ethyl acetate. The organic solution was dried over magnesium sulfate and evaporated to an oil which was chromatographed on silica gel, eluting with a 1:1 mixture of ethyl acetate and hexane. The purified product was stirred with a mixture of ether and hexane and filtered giving ethyl (E)-6-(1,3-dihydro-4-carbamoyl oxy-6-methoxy-7-methyl-3-oxo-5-iso benzofuranyl)-4-methyl-4-thiohexenoate, mp 145°–147° C.

(b) Following the procedure described in paragraph (a) above, but using the appropriate compounds of Formula C and Formula D1, the following compounds of Formula IIB were prepared:

Benzyl (E)-6-(1,3-dihydro-4-carbamoyloxy-6-methoxy-7-methyl-3-oxo-5-isobenzofuranyl)-4-methyl-4-thiohexenoate, m.p. 119°–121° C.

Ethyl (E)-6-{1,3-dihydro-4-[N-(4-carboxyphenyl)-carbamoyloxy]-6-methoxy-7-methyl-3-oxo-5-isobenzofuranyl}-4-methyl-4-thiohexenoate, m.p. 204°–206° C.

Cyclohexyl (E)-6-{1,3-dihydro-4-[N-(4-carboxyphenyl)-carbamoyloxy]-6-methoxy-7-methyl-3-oxo-5-isobenzofuranyl}-4-methyl-4-thiohexenoate, m.p. 205°–206° C.; and Benzyl (E)-6-{1,3-dihydro-4-[N-(4-carboxyphenyl)carbamoyloxy]-6-methoxy-7-methyl-3-oxo-5-isobenzofuranyl}-4-methyl-4-thiohexenoate, m.p. 185°–187° C.;

(c) In a similar manner, but starting as desired with other appropriate compounds of Formula IIA, and substituting as needed other appropriate compounds of Formula D1, the following representative compounds of Formula IIB, in which X is oxygen and $R^4$, $R^5$, $R^7$ and Y are as defined below, are prepared.

| $R^4$ | $R^5$ | $R^7$ | Y |
|---|---|---|---|
| H | 4-carboxyphenyl | phenyl | O |
| H | 4-carboxyphenyl | 4-methoxyphenyl | O |
| H | 4-carboxyphenyl | benzyl | S |
| H | H | methyl | S |
| H | H | cyclohexyl | O |
| H | H | isopropyl | O |
| H | CH₃ | n-butyl | O |
| H | n-propyl | n-entyl | S |
| CH₃ | isobutyl | n-hexyl | O |
| n-hexyl | n-hexyl | cyclohexyl | O |
| methyl | 4-carboxyphenyl | cyclooentyl | O |
| H | 4-methoxycarbonylphenyl | 2-chlorophenyl | S |
| ethyl | 4-carboxyphenyl | 4-chlorophenyl | O |
| H | H | 2,4-dimethyoxy phenyl | O |

(d) Similarly, the following compounds of Formula IIB, in which X is sulfur and $R^4$, $R^5$, $R^7$, and Y are as defined below, are prepared:

| $R^4$ | $R^5$ | $R^7$ | Y |
|---|---|---|---|
| H | 4-carboxyphenyl | phenyl | O |
| H | 4-carboxyphenyl | 4-methoxyphenyl | O |
| H | 4-carboxyphenyl | benzyl | S |
| H | H | methyl | S |
| H | H | cyclohexyl | O |
| H | H | isopropyl | O |
| H | CH₃ | n-butyl | O |
| H | n-propyl | n-entyl | S |
| CH₃ | isobutyl | n-hexyl | O |
| n-hexyl | n-hexyl | cyclohexyl | O |
| methyl | 4-carboxyphenyl | cyclooentyl | O |
| H | 4-methoxycarbonylphenyl | 2-chlorophenyl | S |
| ethyl | 4-carboxyphenyl | 4-chlorophenyl | O |
| H | H | 2,4-dimethyoxy phenyl | O |

EXAMPLE 3

Preparation of ethyl (E)-6-(1,3-dihydro-4-acetoxy-6-methoxy-7-methyl-3-oxo-5-isobenzofuranyl)-4-methyl-4-thiohexanoate and related compounds of Formula IIC and IID (a) To a solution of 1.6 g of ethyl (E)-6-(1,3-dihydro-4-hydroxy-6-methoxy-7-methyl-3-oxo-5-isobenzofuranyl)-4-methyl-4-thiohexenoate in 120 ml of acetonitrile at 0° C. was added 0.74 ml of pyridine followed by 1.0 ml of acetyl chloride. After stirring for 2 hours the reaction mixture was poured into dilute hydrochloric acid and extracted with ethyl acetate. The organic solution was dried over anhydrous magnesium sulfate and evaporated to an oil, which was triturated with ether to give ethyl (E)-6-(1,3-dihydro-4-acetoxy-6-methoxy-7-methyl-3-oxo-5-isobenzofuranyl)-4-methyl-4-thiohexenoate, m.p. 81°–84° C.

(b) Following the procedure described in paragraph (a) above but using mycophenolic acid in place of the compound of Formula IIA and the appropriate acyl halide of Formula D5, the following compounds of Formula IID were prepared:

(E)-6-[1,3-dihydro-4-(carboethoxycarbonyloxy)-6-methoxy-7-methyl-3-oxo-5-isobenzofuranyl]-4-methyl-4-hexenoate, m.p. 125°–127° C.

(E)-6-[1,3-dihydro-4-(carbomethoxyethanoyloxy)-6-methoxy-7-methyl-3-oxo-5-isobenzofuranyl]-4-methyl-4-hexenoate, m.p. 112°–114° C.

(E)-6-[1,3-dihydro-4-(carboethoxyethanoyloxy)-6-methoxy-7-methyl-3-oxo-5-isobenzofuranyl]-4-methyl-4-hexenoate, m.p. 99°–101° C.

(E)-6-[1,3-dihydro-4-(3-carbomethoxypropionyloxy)-6-methoxy-7-methyl-3-oxo-5-isobenzofuranyl]-4-methyl-4-hexanoate, m.p., 125°–127° C.

(E)-6-[1,3-dihydro-4-(3-carboethoxypropionyloxy)-6-methoxy-7-methyl-3-oxo-5-isobenzofuranyl]-4-methyl-4-hexanoate, m.p. 93°–95° C.

(E)-6-[1,3-dihydro-4-(4-carbomethoxybutanoyloxy)-6-methoxy-7-methyl-3-oxo-5-isobenzofuranyl]-4-methyl-4-hexanoate, m.p. 65°–67° C.

(E)-6-[1,3-dihydro-4-(5-carbomethoxypentanoyloxy)-6-methoxy-7-methyl-3-oxo-5-isobenzofuranyl]-4-methyl-4-hexanoate, m.p. 99°–101° C.

(c) In a similar manner, the following exemplary compounds of Formula IIC where X is oxygen and $R^2$ and $R^7$ are as defined below are prepared:

| $R^2$ | $R^7$ |
|---|---|
| ethyl | ethyl |
| n-propyl | n-propyl |
| isopropyl | methyl |
| n-butyl | isopropyl |
| isobutyl | n-butyl |
| n-pentyl | n-hexyl |
| n-hexyl | cyclohexyl |
| methyl | cyclopentyl |
| methyl | 2-chlorophenyl |
| methyl | 4-methoxyphenyl |
| methyl | 2,4-dimethoxyphenyl |

(d) In a similar manner the following compounds of Formula IIC where X is sulfur are prepared:

| $R^2$ | $R^7$ |
|---|---|
| ethyl | ethyl |
| n-propyl | n-propyl |
| isopropyl | methyl |
| n-butyl | isopropyl |
| isobutyl | n-butyl |
| n-pentyl | n-hexyl |
| n-hexyl | cyclohexyl |
| methyl | cyclopentyl |
| methyl | 2-chlorophenyl |
| methyl | 4-methoxyphenyl |
| methyl | 2,4-dimethoxyphenyl |

(e) In a similar manner, but substituting an appropriate acyl halide of Formula D5 for an acyl halide of Formula D4, and starting with the desired compound of Formula IIA, the following compounds of Formula IID where X is oxygen and $R^3$ and $R^7$ are as defined below, are prepared:

| $R^3$ | $R^7$ |
|---|---|
| ethyl | ethyl |
| n-propyl | n-propyl |
| isopropyl | methyl |
| n-butyl | isopropyl |
| isobutyl | n-butyl |
| sec-butyl | n-pentyl |
| n-pentyl | n-hexyl |
| n-hexyl | cyclohexyl |
| methyl | cyclopentyl |
| methyl | 2-chlorophenyl |
| methyl | 4-methoxyphenyl |
| methyl | 2,4-dimethoxyphenyl |

(f) In a similar manner, the following compounds of Formula IID where X is sulfur, are prepared:

| $R^3$ | $R^7$ |
|---|---|
| ethyl | ethyl |
| n-propyl | n-propyl |
| isopropyl | methyl |
| n-butyl | isopropyl |
| isobutyl | n-butyl |
| sec-butyl | n-pentyl |
| n-pentyl | n-hexyl |
| n-hexyl | cyclohexyl |
| methyl | cyclopentyl |
| methyl | 2-chlorophenyl |
| methyl | 4-methoxyphenyl |
| methyl | 2,4-dimethoxyphenyl |

EXAMPLE 4

Preparation of methyl E-6-[1,3-dihydro-4-(1,2-dicarbomethoxy-2-(E)-enyloxy)-6-methoxy-7-methyl-3-oxo-5-isobenzofuranyl]-4-methyl-4-hexenoate and related compounds of Formula IIE (a) To a solution of 6.72 g of methyl E-6-(1,3-dihydro-4-hydroxy-6-methoxy-7-methyl-3-oxo-5-isobenzofuranyl)-4-methyl-4-hexenoate in 100 ml of tetrahydrofuran at −80° C. was added 3.16 ml of pyridine and 4.8 g of dimethyl acetylenedicarboxylate and the mixture was allowed to warm to 25° C. and was stirred for 16 hours. The solution was poured into dilute hydrochloric acid and extracted with diethyl ether. The organic solution was dried over anhydrous sodium sulfate and the solvent removed under reduced pressure. The residue was chromatographed on silica gel eluting with diethyl ether. The purified product was recrystallized from diethyl ether/hexane mixture, to yield methyl E-6-[1,3-dihydro-4-(1,2-dicarbomethoxyeth-2-(E)-enyloxy)-6-methoxy-7-methyl-3-oxo-5-isobenzofuranyl]-4-methyl-4-hexenoate, m.p. 105°–107° C.

(b) Following the procedure described in paragraph (a) above, but substituting as desired the appropriate compounds of Formula IIA and the appropriately substituted acetylenes of Formula D6 for those used in paragraph (a), the following compound of Formula IIE was prepared:

Methyl-E-6-[1,3-dihydro-4-(1,2-dicarboethoxyeth-2-(E)-enyloxy)-6-methoxy-7-methyl-3-oxo-5-isobenzofuranyl]-4-methyl-4-hexenoate, m.p. 61°–63° C.

(c) In a similar manner, the following exemplary compounds of Formula IIE where X is oxygen and $R^3$ and $R^7$ are as defined below are prepared:

| $R^3$ | $R^7$ |
|---|---|
| ethyl | H |
| n-propyl | propyl |
| ethyl | isopropyl |
| methyl | n-butyl |
| methyl | sec-butyl |
| ethyl | n-pentyl |
| n-butyl | n-hexyl |
| isobutyl | cyclohexyl |
| n-pentyl | cyclopentyl |
| methyl | phenyl |
| ethyl | 2-chlorophenyl |
| methyl | 4-chlorophenyl |
| ethyl | 4-methoxyphenyl |
| methyl | 2,4-dimethoxyphenyl |
| ethyl | benzyl |

(d) In a similar manner, but starting instead with the appropriate compounds of Formula IIA in which X is sulfur, the following exemplary compounds of Formula IIE are prepared:

| $R^3$ | $R^7$ |
|---|---|
| n-propyl | propyl |
| ethyl | isopropyl |
| methyl | n-butyl |
| methyl | sec-butyl |
| ethyl | n-pentyl |
| n-butyl | n-hexyl |
| isobutyl | cyclohexyl |
| n-pentyl | cyclopentyl |
| methyl | phenyl |
| ethyl | 2-chlorophenyl |
| methyl | 4-chlorophenyl |
| ethyl | 4-methoxyphenyl |
| methyl | 2,4-dimethoxyphenyl |
| ethyl | benzyl |

EXAMPLE 5

Preparation of
(E)-6-[1,3-dihydro-4-(1,2-dicarboxyeth-2-(E)-enyloxy)-6-methoxy-7-methyl-3-oxo-5-isobenzofuranyl]-4-methyl-4-hexenoic acid, a Compound of Formula IIF (a) To a solution of 2.4 g of methyl (E)-6-[1,3-dihydro-4-(1,2-dicarbomethoxy 2(E)-enyloxy)-6-methoxy-7-methyl-3-oxo-5-isobenzofuranyl]-4-methyl-4-hexenoate in 50 ml of tetrahydrofuran was added a solution of 1.2 g of lithium hydroxide monohydrate in 50 ml of water. After stirring for 20 hours the solution was poured into dilute hydrochloric acid and extracted with ethyl acetate. The organic layer was dried over anhydrous sodium sulfate and the solvent removed under reduced pressure. The residue was chromatographed on silica gel, eluting with 0.1% formic acid in ethyl acetate. The purified product was triturated with ether, giving (E)-6-[1,3-dihydro-4-(1,2-dicarboxyeth-2(E)-enyloxy)-6-methoxy-7-methyl-3-oxo-5-isobenzofuranyl]-4-methyl-4-hexenoic acid, m.p. 203°–205° C.

(b) Following the procedure described in paragraph (a) above, but starting with the appropriate compound of Formula IIE, the following compound of Formula IIF was prepared:
(E)-6-[1,3-dihydro-4-(E)(2-carboxy-ether-1-gloxy)-6-methoxy-7-methyl-3-oxo-5-isobenzofuranyl]-4-methyl-4-hexenoic acid, m.p. 145°–146° C.

(c) In a similar manner, but starting as desired with other appropriate compounds of Formulas IIE and D6, the following compounds of Formula IIF in which X is oxygen and R, Q and $R^7$ are as defined below are prepared:

| R | Q | $R^7$ |
|---|---|---|
| H | $CO_2CH_3$ | phenyl |
| H | $CO_2C_2H_5$ | 4-methoxyphenyl |
| H | $CO_2$isopropyl | benzyl |
| H | $CO_2$n-propyl | methyl |
| H | $CO_2$sec-butyl | cyclohexyl |
| H | $CO_2$n-butyl | isopropyl |
| H | $CO_2$n-pentyl | n-butyl |
| $CO_2CH_3$ | H | n-pentyl |
| $CO_2C_2H_5$ | H | n-hexyl |
| $CO_2$isopropyl | H | cyclohexyl |
| $CO_2$n-propyl | H | cyclopentyl |
| $CO_2$sec-butyl | H | 2-chlorophenyl |
| $CO_2$n-butyl | H | 4-chlorophenyl |
| $CO_2$n-pentyl | H | 2,4-dimethoxyphenyl |
| $CO_2CH_3$ | $CO_2CH_3$ | n-pentyl |
| $CO_2C_2H_5$ | $CO_2C_2H_5$ | n-hexyl |
| $CO_2$isopropyl | $CO_2$isopropyl | cyclohexyl |
| $CO_2$n-propyl | H | cyclopentyl |
| $CO_2$sec-butyl | H | 2-chlorophenyl |
| $CO_2$n-butyl | H | 4-chlorophenyl |
| $CO_2$n-pentyl | H | 2,4-dimethoxyphenyl |

(d) In a similar manner, but starting as desired with other appropriate compounds of Formulas IIE and D6, the following exemplary compounds of Formula IIF in which X is sulfur and R, Q and $R^7$ are as defined below are prepared:

| R | Q | $R^7$ |
|---|---|---|
| H | $CO_2CH_3$ | phenyl |
| H | $CO_2C_2H_5$ | 4-methoxyphenyl |
| H | $CO_2$isopropyl | benzyl |
| H | $CO_2$n-propyl | methyl |
| H | $CO_2$sec-butyl | cyclohexyl |
| H | $CO_2$n-butyl | isopropyl |
| H | $CO_2$n-pentyl | n-butyl |
| $CO_2CH_3$ | H | n-pentyl |
| $CO_2C_2H_5$ | H | n-hexyl |
| $CO_2$isopropyl | H | cyclohexyl |
| $CO_2$n-propyl | H | cyclopentyl |
| $CO_2$sec-butyl | H | 2-chlorophenyl |
| $CO_2$n-butyl | H | 4-chlorophenyl |
| $CO_2$n-pentyl | H | 2,4-dimethoxyphenyl |
| $CO_2CH_3$ | $CO_2CH_3$ | n-pentyl |
| $CO_2C_2H_5$ | $CO_2C_2H_5$ | n-hexyl |
| $CO_2$isopropyl | $CO_2$isopropyl | cyclohexyl |
| $CO_2$n-propyl | H | cyclopentyl |
| $CO_2$sec-butyl | H | 2-chlorophenyl |
| $CO_2$n-butyl | H | 4-chlorophenyl |
| $CO_2$n-pentyl | H | 2,4-dimethoxyphenyl |

EXAMPLE 6

Conversion of Free Acid to Salt

One molar equivalent of sodium hydroxide in water is added to a methanolic solution of 1.0 g of (E)-6-[1,3-dihydro-4(3-carboethoxypropionyloxy)-6-methoxy-7-methyl-3-oxo-5-isobenzoylfuranyl]-4-methyl-4-hexenoic acid. The solvent is removed under vacuum and the residue recrystallized to give the sodium salt of (E)-6-[1,3-dihydro-4(3-carboethoxypropionyloxy)-6-methoxy-7-methyl-3-oxo-5-isobenzoylfuranyl]-4-methyl-4-hexenoic acid.

EXAMPLE 7

Conversion of Salt to Free Acid 1.0 g of the sodium salt of (E)-6-[1,3-dihydro-4(3-carboethoxypropionyloxy)-6-methoxy-7-methyl-3-oxo-5-isobenzoylfuranyl]-4-methyl-4-hexenoic acid suspended in ether is stirred with 2 molar equivalents of dilute aqueous sulfuric acid until the salt is completely dissolved. The organic layer is separted, washed with water, dried over magnesium sulfuate and evaporated to yield (E)-6-[1,3-dihydro-4(3-carboethoxypropionyloxy)-6-methoxy-7-methyl-3-oxo-5-isobenzoylfuranyl]-4-methyl-4-hexenoic acid.

EXAMPLE 8

Direct Interchange of Basic Salts 1.0 g of the ammonium salt of (E)-6-[1,3-dihydro-4(3-carboethoxypropionyloxy)-6-methoxy-7-methyl-3-oxo-5-isobenzoylfuranyl]-4-methyl-4-hexenoic acid is dissolved in methanol containing one molar equivalent of sodium hydroxide and the solution evaporated to dryness under vacuum. The residue is recrystallized to give the sodium salt of (E)-6-[1,3-dihydro-4(3-carboethoxypropionyloxy)-6-methoxy-7-methyl-3-oxo-5-isobenzoylfuranyl]-4-methyl-4-hexenoic acid.

EXAMPLES 9–13

In Examples 5 through 9, the active ingredient is (E)-6-[1,3-dihydro-4(3-carboethoxypropionyloxy)-6-methoxy-7-methyl-3-oxo-5-isobenzoylfuranyl]-4-methyl-4-hexenoic acid. However other compounds of Formula I and II such as those prepared in Examples 1–5, and the pharmaceutically acceptable salts thereof may be substituted:

EXAMPLE 9

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 10

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 11

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 12

| Ingredients | Quantity per tablet, mgs. |
| --- | --- |
| Active ingredient | 150 |
| lactose | 92 |

The above ingredients are mixed and introduced into a hard-shell gelatin capsule.

EXAMPLE 13

A solution preparation buffered to a pH of 7 is prepared having the following composition:

| Ingredients | |
| --- | --- |
| Active ingredient | 0.1 g |

| Ingredients | |
| --- | --- |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| distilled water | q.s. to 100 ml |

EXAMPLE 14

Determination of Anti-Inflammatory Activity Utilizing Adjuvant-Induced Arthritis In The Rat Protocol:

This procedure is a modification of a system initially described by Pearson, C. M., *Proc. Soc. Exp. Biol. Med.*, 91:95–101 (1956).

Female Crl:CD, br (Sprague Dowley derived) rats (Charles River) weighing 165–185 g receive 0.1 ml of a suspension in paraffin oil of heat-killed M. *Mycobacterium butyricum* (10 mg/ml) by means of an intradermal injection into the proximal ¼ of the tail on day 0. Beginning on day 1, the test material is administered orally in an aqueous vehicle (1 ml/dose) once a day for 17 days. On day 18 the intensity of the swelling of the four foot pads and tail is determined utilizing a scoring system in which the swelling in the four paws was scored 0–4 for each paw and the tail swelling was scored 0–3, such that the total maximum score is 19. The compounds of the present invention show anti-inflammatory activity when tested by this method.

EXAMPLE 15

DETERMINATION OF AUTOIMMUNE ACTIVITY UTILIZING EXPERIMENTAL ALLERGIC ENCEPHALOMYELITIS

Protocol:

This procedure is a modification of a procedure initially described by Grieg, et al., *J. Pharmacol. Exp. Ther.* 173:85 (1970). Female Lewis rats, LEW/Cre, br from Charles River, weighing 125–135 g were used.

On day 1, Experimental Allergic Encephalomyelitis is induced by giving an 0.1 ml sub-plantar injection into the dorsum of the right hind paw of an emulsion consisting of 15 mg (wet weight) of syngeneic spinal cord tissue, 0.06 ml of Freund's Incomplete Adjuvant (Difco). 0.04 ml of sterile 0.9% saline, and 0.2 mg of heat killed and dried *Mycobacterium butyricum* (Difco). Beginning on day 1, the test material is administered orally in 2N aqueaus vehicle (1 ml/dose) once a day for 16 days. On days 12–17, clinical evaluations are obtained for each animal. The animals are considered positive if flaccid hind limb paralysis is present on one or more days. The compounds of the present invention show autoimmune activity when tested by this method.

What is claimed is:

1. A compound of the formula:

(II)

[chemical structure showing compound with $OR^1$, $OCH_3$, $CH_3$, and $CXR^7$ groups]

or a pharmaceutically acceptable salt thereof, wherein:
R¹ is selected from the group consisting of

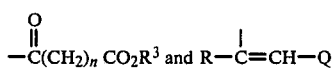

in which n is an integer from 0-2;

R³ is H, alkyl having 1 to 6 carbon atoms or a pharmaceutically acceptable cation;

Q and R are each H or —$CO_2R^3$;

X is oxygen or sulfur; and

R⁷ is H, alkyl having 1 to 6 carbon atoms, cycloalkyl of 5 to 7 carbon atoms, phenyl or benzyl wherein the phenyl ring of the phenyl or benzyl group is optionally substituted by one or two substituents independently chosen from lower alkyl of 1 to 4 carbon atoms, halo or hydroxy, or a pharmaceutically acceptable cation.

2. The compound of claim 1, or a pharmaceutically acceptable salt thereof, in which X is oxygen.

3. The compound of claim 2, or a pharmaceutically acceptable salt thereof, in which $R^7$ is hydrogen or methyl.

4. The compound of claim 3, or a pharmaceutically acceptable salt thereof, in which $R_1$ is $CO(CH_2)_nCO_2R^3$.

5. The compound of claim 4, or a pharmaceutically acceptable salt thereof, in which $R^3$ is methyl or ethyl.

6. The compound of claim 5, wherein n is 2, $R^7$ is hydrogen, and $R^3$ is methyl, namely (E)-6-[1,3-dihydro-4-(3-carbomethoxypropionyloxy)-6-methoxy-7-methyl-3-oxo-5-isobenzofuranyl]-4-methyl-4-hexenoic acid.

7. The compound of claim 5 in which n is 2, $R^7$ is hydrogen and $R^3$ is ethyl, namely (E)-6-[1,3-dihydro-4-(3-carboethoxypropionyloxy)-6-methoxy-7-methyl-3-oxo-5-isobenzofuranyl]-4-methyl-4-hexenoic acid.

8. The compound of claim 5 in which n is 1, $R^7$ is hydrogen and $R^3$ is methyl, namely (E)-6-[1,3-dihydro-4-(2-carbomethoxyethanoyloxy)-6-methoxy-7-methyl-3-oxo-5-isobenzofuranyl]-4-methyl-4-hexenoic acid.

9. The compound of claim 3, or a pharmaceutically acceptable salt thereof, in which $R^1$ is R—C=CH—Q.

10. The compound of claim 9 or a pharmaceutically acceptable salt thereof, in which R and Q are each $CO_2R^3$ where $R^3$ is hydrogen, methyl or ethyl.

11. The compound of claim 10, or a pharmaceutically acceptable salt thereof, in which $R^7$ is methyl and each $R^3$ is methyl, namely, methyl (E)-6-[1,3-dihydro-4-(1,2-dicarbomethoxyeth-2-(E)-enyloxy)-6-methoxy-7-methyl-3-oxo-5-isobenzofuranyl]-4-methyl-4-hexenoate.

12. The compound of claim 10, or a pharmaceutically acceptable salt thereof, in which $R^7$ is methyl and each $R^3$ is ethyl, namely, methyl (E)-6-[1,3-dihydro-4-(1,2-dicarboethoxyeth-2-(E)-enyloxy)-6-methoxy-7-methyl-3-oxo-5-isobenzofuranyl]-4-methyl-4-hexenoate.

13. The compound of claim 1, or a pharamaceutically acceptable salts thereof, in which X is sulfur.

14. A pharmaceutical composition for treating rheumatoid arthritis which comprises a therapeutically effective amount of a compound of claim 1, in admixture with one or more pharmaceutically acceptable excipients.

15. A method of treating rheumatoid arthritis which method comprises administering to a mammal in need of such treatment a therapeutically effective amount of a compound of claim 1, or a pharmaceutically acceptable salt thereof.

* * * * *